(12) United States Patent
Nakamura

(10) Patent No.: US 11,382,645 B2
(45) Date of Patent: Jul. 12, 2022

(54) TREATMENT TOOL

(71) Applicant: OLYMPUS CORPORATION, Tokyo (JP)

(72) Inventor: Takashi Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 238 days.

(21) Appl. No.: 16/681,988

(22) Filed: Nov. 13, 2019

(65) Prior Publication Data
US 2020/0078033 A1   Mar. 12, 2020

Related U.S. Application Data

(63) Continuation of application No. PCT/JP2017/018631, filed on May 18, 2017.

(51) Int. Cl.
*A61B 17/29* (2006.01)
*A61B 34/00* (2016.01)
*A61B 90/00* (2016.01)
*A61B 10/06* (2006.01)

(52) U.S. Cl.
CPC .............. *A61B 17/29* (2013.01); *A61B 10/06* (2013.01); *A61B 34/71* (2016.02); *A61B 90/03* (2016.02); *A61B 2017/2902* (2013.01); *A61B 2017/2905* (2013.01); *A61B 2090/034* (2016.02)

(58) Field of Classification Search
CPC ......... A61B 17/29; A61B 34/71; A61B 90/03; A61B 10/06; A61B 2090/034; A61B 2017/2902; A61B 2017/2905
See application file for complete search history.

(56) References Cited

U.S. PATENT DOCUMENTS

2005/0090837 A1   4/2005  Sixto et al.
2006/0217743 A1   9/2006  Messerly et al.
(Continued)

FOREIGN PATENT DOCUMENTS

CA   2509915 A1   12/2005
EP   1607055 A1   12/2005
(Continued)

OTHER PUBLICATIONS

International Search Report dated Aug. 8, 2017 issued in PCT/JP2017/018631.

*Primary Examiner* — Brooke Nicole Labranche
(74) *Attorney, Agent, or Firm* — Scully, Scott, Murphy & Presser, P.C.

(57) ABSTRACT

Provided is a treatment tool including an elongated inserting section that is curveable or bendable, a wire that is disposed from an end effector to a proximal end side of the inserting section through the inserting section, the end effector being connected to a tip of the inserting section, and a power input section that is disposed on the proximal end side of the inserting section and configured to input power to a proximal end portion of the wire, and the wire transmits, to the end effector, power to drive the end effector, and the power input section is configured to increase the power to be input into the proximal end portion of the wire in response to displacement of the proximal end portion of the wire in a longitudinal direction, the displacement accompanying a curve or bend of the inserting section.

15 Claims, 17 Drawing Sheets

(56) References Cited

U.S. PATENT DOCUMENTS

| | | | | |
|---|---|---|---|---|
| 2006/0258954 A1* | 11/2006 | Timberlake | ............ | A61B 10/06 600/564 |
| 2010/0268254 A1* | 10/2010 | Golden | .............. | A61B 17/1285 606/142 |
| 2011/0106141 A1 | 5/2011 | Nakamura | | |
| 2011/0288579 A1 | 11/2011 | Hyodo | | |
| 2013/0046338 A1 | 2/2013 | Suzuki et al. | | |

FOREIGN PATENT DOCUMENTS

| | | |
|---|---|---|
| EP | 1707129 A1 | 10/2006 |
| EP | 2305144 A1 | 4/2011 |
| EP | 2554129 A1 | 2/2013 |
| JP | 2006-634 A | 1/2006 |
| JP | 2006-271975 A | 10/2006 |
| JP | 2011-239922 A | 12/2011 |
| JP | 4954501 B2 | 6/2012 |
| JP | 2013-215507 A | 10/2013 |
| WO | WO 2010/109932 A1 | 9/2010 |
| WO | WO 2012/118011 A1 | 9/2012 |

* cited by examiner

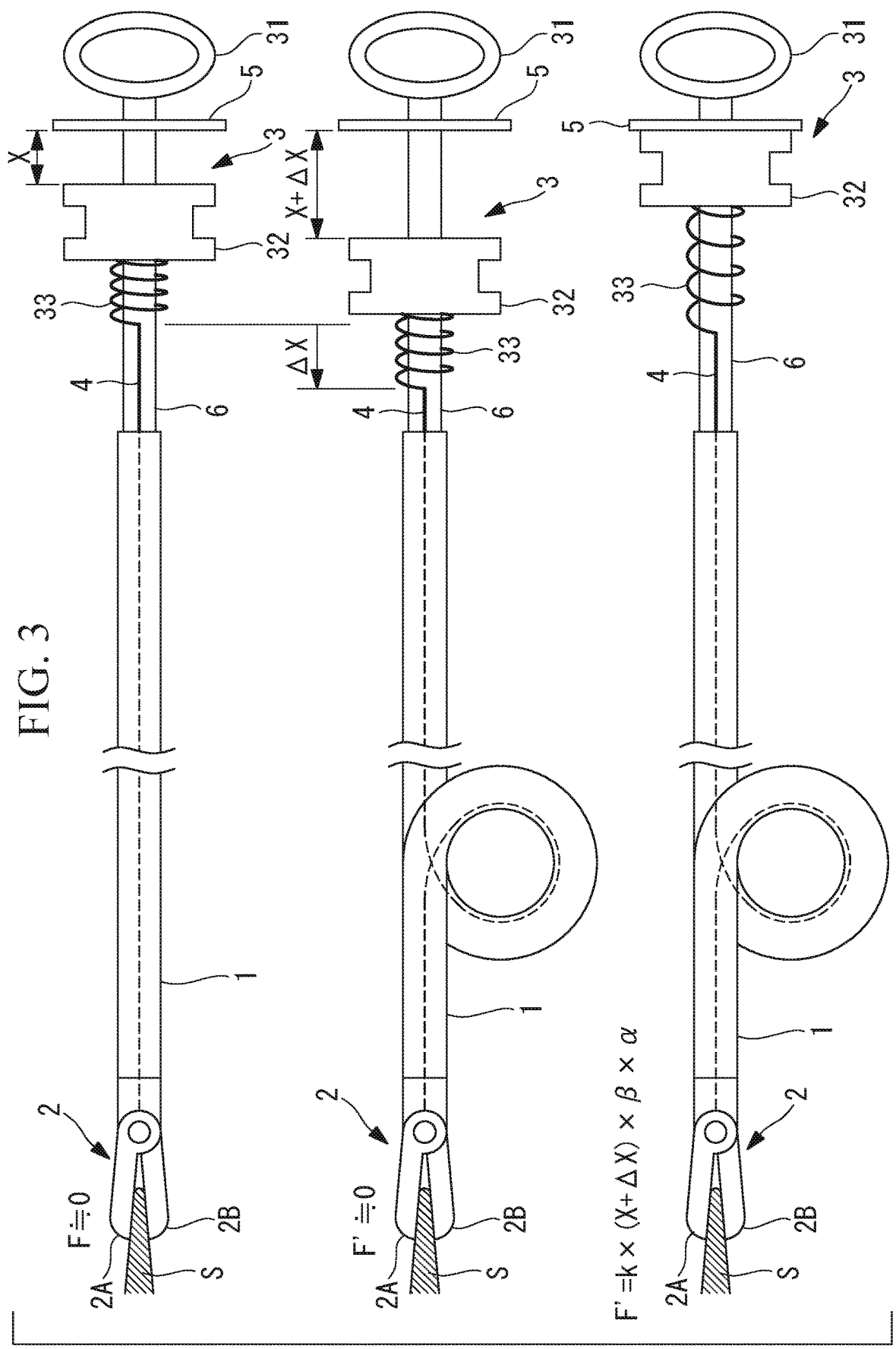

TREATMENT TOOL

CROSS-REFERENCE TO RELATED APPLICATIONS

This is a continuation of International Application PCT/JP2017/018631 which is hereby incorporated by reference herein in its entirety.

TECHNICAL FIELD

The present invention relates to a treatment tool.

BACKGROUND ART

Heretofore, there has been known a treatment tool provided with a mechanism that limits power to be transmitted to an end effector such as a pair of forceps (e.g., see PTL 1). The treatment tool of PTL 1 includes an operating wire connected to the end effector, a slider for an operator to pull the operating wire, and an elastic body that connects the operating wire to the slider. The elastic body is deformed by retraction of the slider, and further retraction of the slider is stopped by the deformed elastic body. Thus, a pulling force that acts on the operating wire is limited. Consequently, a grip force of the pair of forceps that is the end effector can be limited to a value that is less than or equal to a predetermined value.

CITATION LIST

Patent Literature

{PTL 1}
PCT International Publication No. WO 2012/118011

SUMMARY OF INVENTION

According to an aspect of the present invention, a treatment tool includes an elongated inserting section that is curveable or bendable; a wire that is disposed from an end effector to a proximal end side of the inserting section through the inserting section, the end effector being connected to a tip of the inserting section; and a power input section that is disposed on the proximal end side of the inserting section and configured to input power to a proximal end portion of the wire, wherein the wire transmits, to the end effector, power to drive the end effector, and the power input section is configured to increase the power to be input into the proximal end portion of the wire in response to displacement of the proximal end portion of the wire in a longitudinal direction, the displacement accompanying a curve or bend of the inserting section.

BRIEF DESCRIPTION OF DRAWINGS

FIG. 3 is an explanatory view of a relation between a shape of an inserting section and a position of a proximal end portion of a wire in the treatment tool of FIG. 1, and shows a state where the inserting section linearly extends (an upper illustration), and a state where the inserting section is curved (a middle illustration and a lower illustration).

DESCRIPTION OF EMBODIMENTS

First Embodiment

Description will be hereinafter made as to a treatment tool 100 according to a first embodiment of the present invention with reference to FIG. 1 to FIG. 7B.

Figure 1:
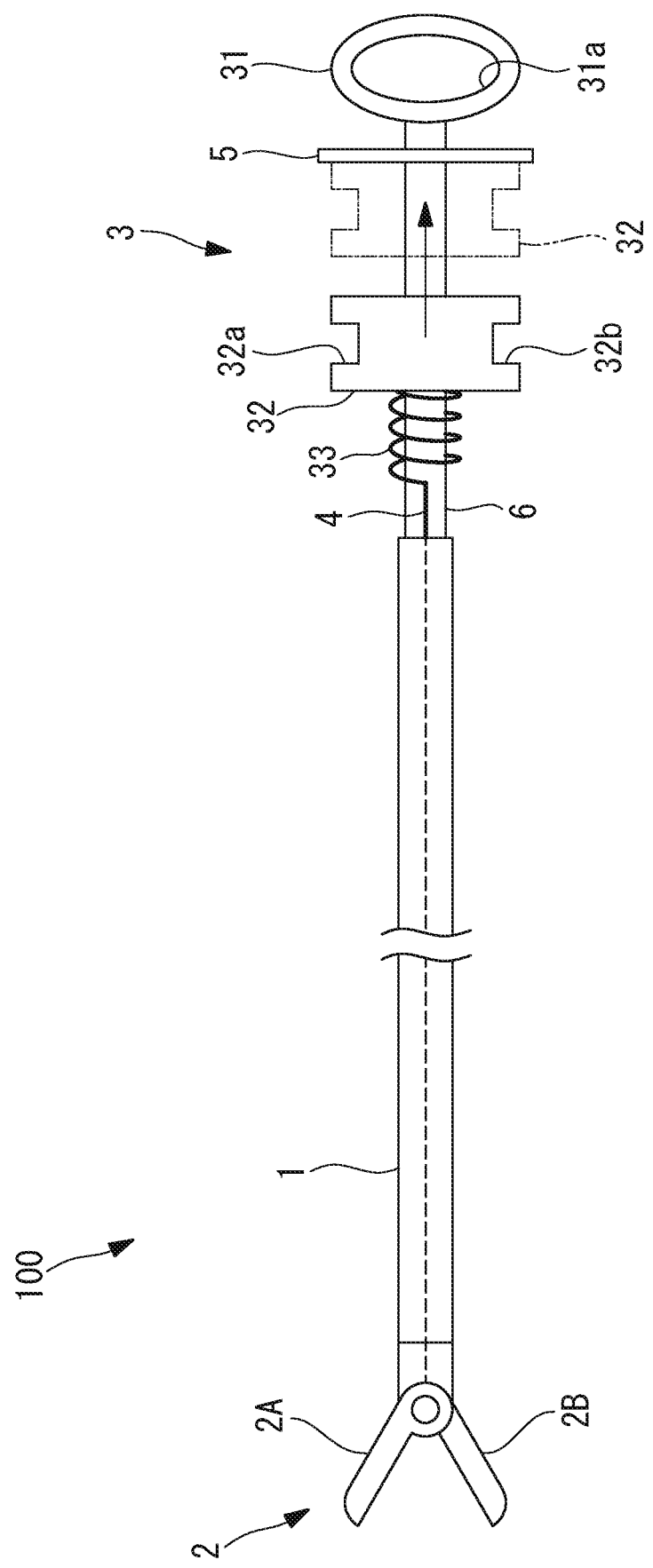
FIG. 1 is an overall configuration view of a treatment tool according to a first embodiment of the present invention.

As shown in FIG. 1, the treatment tool 100 according to the present embodiment includes a flexible elongated inserting section 1, an end effector 2 connected to a tip of the inserting section 1, an operating section (a power input section) 3 that is disposed on a proximal end side of the inserting section 1, and generates power to drive the end effector 2 by an operation of an operator, and a wire (a power transmission member) 4 that extends through the inserting section 1 to connect the end effector 2 to the operating section 3, and transmits the power input from the operating section 3 to the end effector 2.

The inserting section 1 includes a tubular member having flexibility, for example, a coil sheath. In the inserting section 1, the wire 4 is disposed movably in a longitudinal direction. A tip portion of the wire 4 is fixed to the end effector 2, and a proximal end portion of the wire 4 is drawn out from a proximal end of the inserting section 1, and is connected to an elastic member 33 of the operating section 3 as described later. To sufficiently decrease friction between the wire 4 and a peripheral member in the inserting section 1, a treatment to increase slidability is performed on the surface of the wire 4. For example, the surface of the wire 4 is coated with a high slidability material (a low friction material), or lubricant is applied to the surface.

The end effector 2 includes a pair of grip forceps having grip pieces 2A, 2B that are openable and closable to each other. The end effector 2 is configured to open by a pressing force (power) applied from the wire 4 toward a tip side, and to close by a pulling force (the power) applied from the wire 4 toward the proximal end side. Therefore, a size of a grip force generated by the end effector 2 is controlled by the pulling force from the wire 4.

Note that the end effector 2 is not limited to the pair of grip forceps, and another type of end effector (e.g., a knife) that receives power to perform a mechanical operation may be adopted. Alternatively, the end effector 2 may be configured so that a joint provided in the end effector 2 is driven by the power from the wire 4.

The operating section 3 includes an operating section main body 31 fixed to the inserting section 1, a slider (an operation member) 32 that is movable in a direction along the longitudinal direction of the inserting section 1 between the inserting section 1 and the operating section main body 31, and an elastic member 33 disposed between a proximal end portion of the wire 4 and the slider 32 to connect the proximal end portion of the wire 4 to the slider 32.

The operating section main body 31 is fixed to an end portion of a columnar connection member 6 extending from the proximal end of the inserting section 1 to the proximal end side (a side opposite to the tip of the inserting section 1) along the longitudinal direction of the inserting section 1. In the operating section main body 31, a hole 31a is provided in which a thumb can be inserted, and in the slider 32, grooves 32a, 32b are provided that receive an index finger and a middle finger, respectively. The operator inserts the thumb in the hole 31a of the operating section main body 31, and places the index finger and the middle finger in the grooves 32a and 32b, respectively, to grip the slider 32 between the index finger and the middle finger. The operator moves the index finger and the middle finger in a direction away from the thumb to advance the slider 32 to the tip side, and moves the index finger and the middle finger in a direction close to the thumb, so that the slider 32 can be retracted to the proximal end side (an operating section main body 31 side).

A movement amount of the slider 32 to the proximal end side is limited by a movement regulating section 5 including a member disposed between the slider 32 and the operating section main body 31 and fixed to the operating section main body 31. The slider 32 can retract back to a movement limit position at which the slider abuts on the movement regulating section 5.

The elastic member 33 is, for example, a coil spring, and is disposed on an outer side of the connection member 6 to expand and contract in the longitudinal direction of the inserting section 1. A tip portion of the elastic member 33 is fixed to the proximal end portion of the wire 4, and a proximal end portion of the elastic member 33 is fixed to the slider 32.

Figure 2:
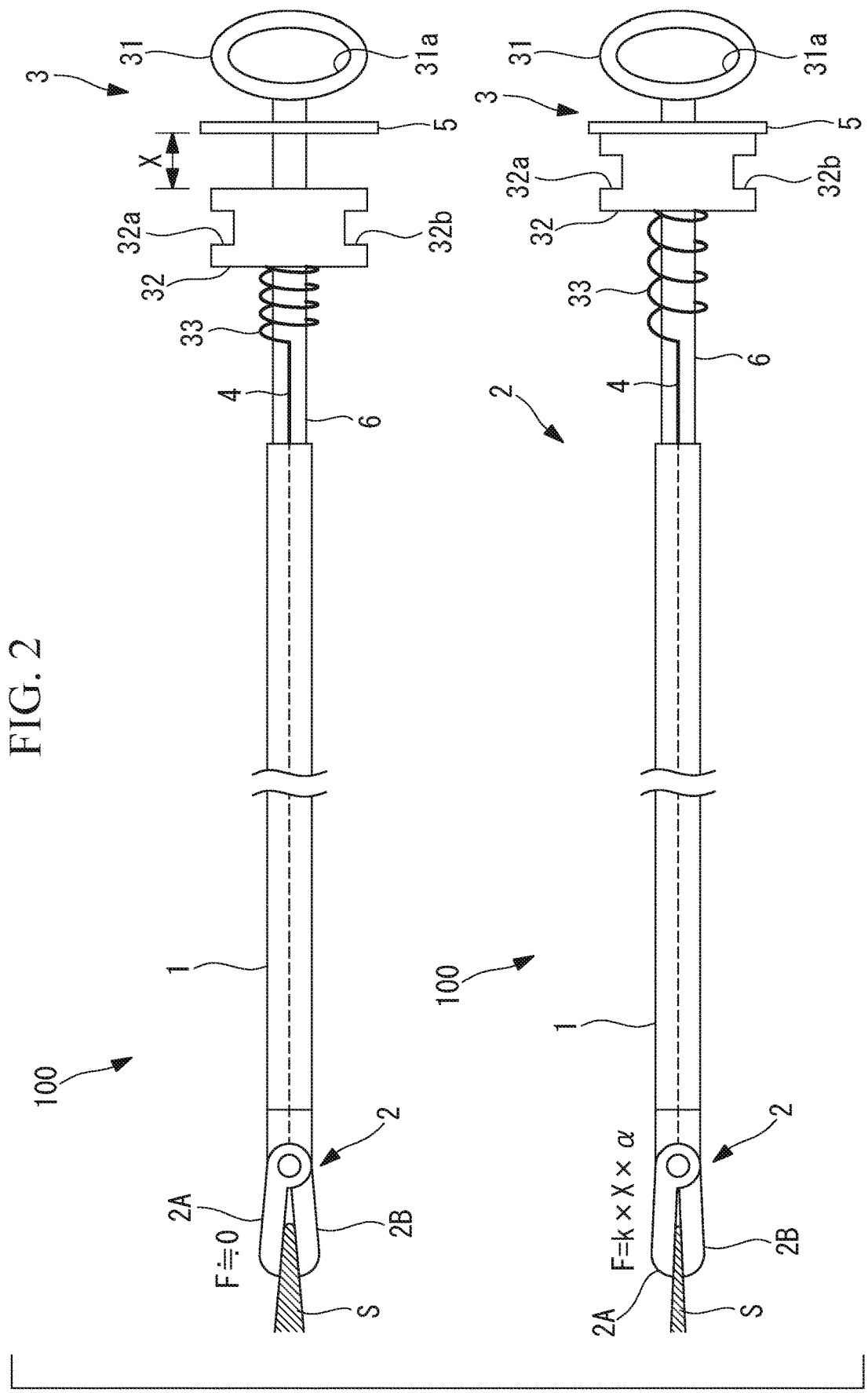
FIG. 2 is an explanatory view of a relation between an operation of a slider and a grip force of an end effector in the treatment tool of FIG. 1, and shows a state where the end effector is lightly closed (an upper illustration) and a state where the end effector is tightly closed and exerts a grip force (a lower illustration).

FIG. 2 shows a relation between movement of the slider 32 and the grip force generated by the end effector 2. As shown in FIG. 2, the slider 32 is movable between a closed position to close the end effector 2 (see an upper illustration of FIG. 2) and the movement limit position located closer to a proximal end side than the closed position and allowing the end effector 2 to exert a predetermined amount of grip force (see a lower illustration of FIG. 2).

When the slider 32 is disposed at the closed position, the pulling force is input into the proximal end portion of the wire 4 toward the proximal end side via the elastic member 33 having a natural length. The pulling force is transmitted to the end effector 2 through the wire 4, to close the end effector 2. In this state, the grip pieces 2A, 2B are only lightly in contact with each other, and a grip force F is hardly generated between the grip piece 2A and the grip piece 2B.

When the slider 32 moves from the closed position toward the movement limit position, a position of the proximal end portion of the wire 4 does not change, and the elastic member 33 elongates. The elongated elastic member 33 generates an elastic force toward the proximal end side. This elastic force is input as the pulling force into the proximal end portion of the wire 4, and the grip force is accordingly generated in the end effector 2. Note that the wire 4 is not extended by the pulling force, or extends only negligibly. Furthermore, when the slider 32 is disposed at the movement limit position, the elastic member 33 elongates up to a maximum amount to maximize the pulling force to be input into the proximal end portion of the wire 4, and the grip force F of the end effector 2 is maximized.

Here, as shown in FIG. 3, when the inserting section 1 is deformed between a linear shape and a curved shape, the wire 4 is displaced in the longitudinal direction within the inserting section 1, thereby displacing the elastic member 33 and the slider 32 in the longitudinal direction. When the closed position is displaced by the displacement of the slider 32, and when the slider 32 is retracted from the closed position to the movement limit position, the pulling force to be input into the proximal end portion of the wire 4 is maximized. In FIG. 3, X indicates a movement amount (an operation amount) of the slider 32 from the closed position to the movement limit position, when the inserting section 1 has the linear shape.

Specifically, in a state where the inserting section 1 is curved (see a middle illustration of FIG. 3), as compared with a state where the inserting section 1 linearly extends (see an upper illustration of FIG. 3), each of the proximal end portion of the wire 4, the elastic member 33 and the slider 32 is displaced as much as $\Delta X$ toward the tip side, and the movement amount (a maximum operation amount) of the slider 32 from the closed position to the movement limit position therefore increases as much as $\Delta X$. In consequence, when the slider 32 is disposed at the movement limit position (see a lower illustration of FIG. 3), an elongation amount of the elastic member 33 increases as much as $\Delta X$, and the pulling force applied to the proximal end portion of the wire 4 increases as much as k×ΔX, where k is the spring constant of the elastic member 33.

Figure 4A:
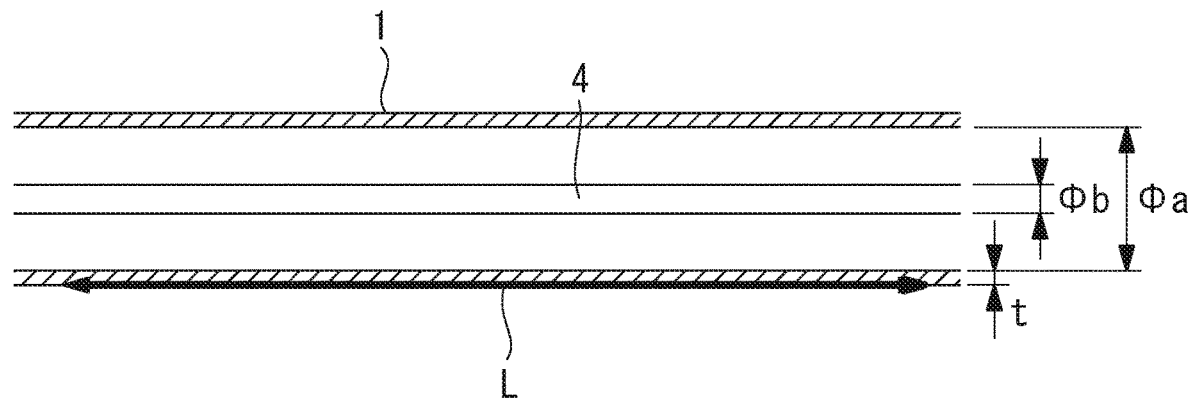
FIG. 4A is an explanatory view of a path length of the wire when the inserting section linearly extends.
Figure 4B:
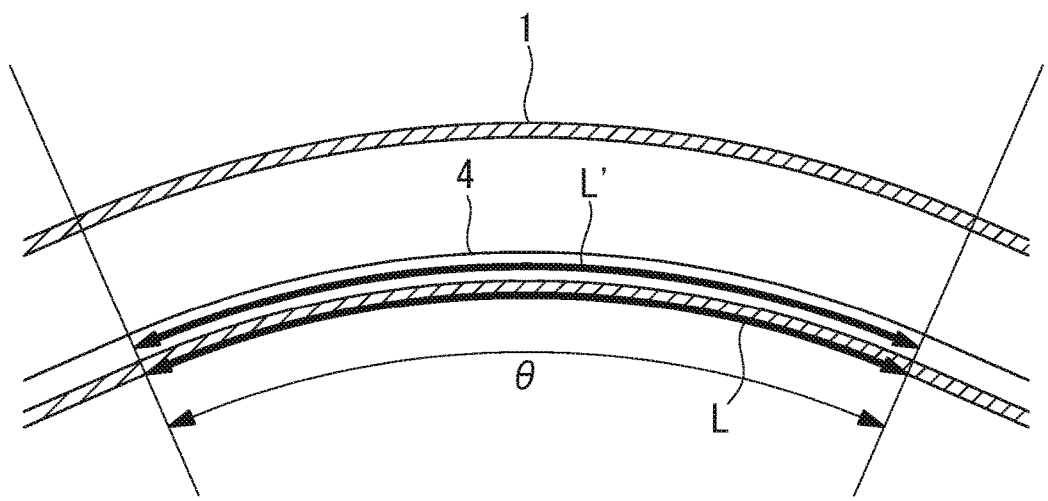
FIG. 4B is an explanatory view of a path length of the wire when the inserting section is curved.

FIG. 4A and FIG. 4B explain a relation between a curve angle θ of the inserting section 1 and a displacement amount ΔX of the proximal end portion of the wire 4. When a part of the inserting section 1 having a length L of the linear shape as shown in FIG. 4A is circularly curved at an angle θ as shown in FIG. 4B, the wire 4 on which the pulling force acts closely contacts an inner surface of the inserting section 1 on an inner side in a radial direction. In case of the inserting section 1 that is hard to compress in the longitudinal direction as in a coil sheath, a length L' of the wire 4 in a curved portion of the inserting section 1 is represented by the following equation, where $\Phi b$ is a diameter of the wire 4, and t is a thickness of a side wall of the inserting section 1.

$$L'=L+(\Phi b/2+t)\times\theta$$

From the above equation, the displacement amount ΔX of the proximal end portion of the wire 4 when the inserting section 1 is curved at the angle θ is represented by $(\Phi b/2+t)\times\theta$. In this way, the displacement amount ΔX of the wire 4 increases linearly in accordance with the curve angle θ of the inserting section 1.

On the other hand, in the state where the inserting section 1 is curved, when the flexible wire 4 in the inserting section 1 is curved, loss is generated in the power to be transmitted through the wire 4 in the longitudinal direction. A power transmission efficiency β of the wire 4 is represented by the following equation from Euler's belt theory.

$$\beta=\exp(-\lambda\theta)\approx 1-\lambda\times\theta$$

Here, a friction coefficient λ of the surface of the wire 4 is sufficiently small, and the power transmission efficiency β can be therefore approximated as in the above equation. That is, the power transmission efficiency β of the wire 4 linearly decreases in accordance with the curve angle θ of the inserting section 1.

A maximum grip force F[N] exerted by the end effector 2 when the inserting section 1 linearly extends and a maximum grip force F'[N] exerted by the end effector 2 when the inserting section 1 is curved are represented by the following equations, respectively, where α indicates a value in which there are taken into account the power transmission efficiency of the wire 4 when the inserting section 1 linearly extends, a power amount transmission efficiency of the end effector 2, and a deceleration rate (a power amount amplification factor) of the end effector 2.

$$F=k\times X\times\alpha$$

$$F'=k\times(X+\Delta X)\times\beta\times\alpha$$

An initial movement amount X is designed as in the following Equation (1) so that the grip forces F and F' are the same (i.e., F=F' is satisfied) when the inserting section 1 extends and when the inserting section is curved.

$$X = \beta \times \Delta X / (1-\beta) \qquad (1)$$
$$= (1-\lambda\theta)(\Phi b/2+t)/\lambda,$$

where $\Phi b$ and t indicate designed values of the wire 4 and the inserting section 1, respectively. The friction coefficient λ is experimentally measured. The curve angle θ of the inserting section 1 is almost constant depending on a procedure, and therefore determined in accordance with the procedure.

Next, an operation of the treatment tool 100 having such a configuration will be described.

To treat a tissue S by use of the treatment tool 100 according to the present embodiment, the operator inserts the inserting section 1 into a body to place the end effector 2 of the tip in a vicinity of the tissue S. Next, the operator advances the slider 32 provided in the operating section 3 from the closed position to open the end effector 2, and holds the tissue S between the pair of pieces of the end effector 2. Next, the operator retracts the slider 32 back to the closed position to close the end effector 2 to lightly grip an affected area therewith. Furthermore, the operator retracts the slider 32 back to the movement limit position to generate a predetermined amount of grip force in the end effector 2, so that the affected area can be tightly gripped with the end effector 2.

In this case, the inserting section 1 is curved in the body, and the power transmission efficiency β of the wire 4 accordingly decreases in proportion to the curve angle θ. On the other hand, in the state where the inserting section 1 is curved, the proximal end portion of the wire 4 is displaced as much as the amount ΔX in proportion to the curve angle θ, and the pulling force generated by the elastic member 33 increases as much as k×ΔX. Thus, the power to be input into the proximal end portion of the wire 4 is increased as much as an amount based on the displacement amount ΔX of the proximal end portion of the wire 4, so that the loss of power due to the decrease of the power transmission efficiency β of the wire 4 can be highly accurately compensated. This has an advantage that irrespective of the curve angle θ of the inserting section 1, a constant amount of power is applied from the tip portion of the wire 4 to the end effector 2, and a constant amount of grip force can be generated in the end effector 2.

Figure 5:
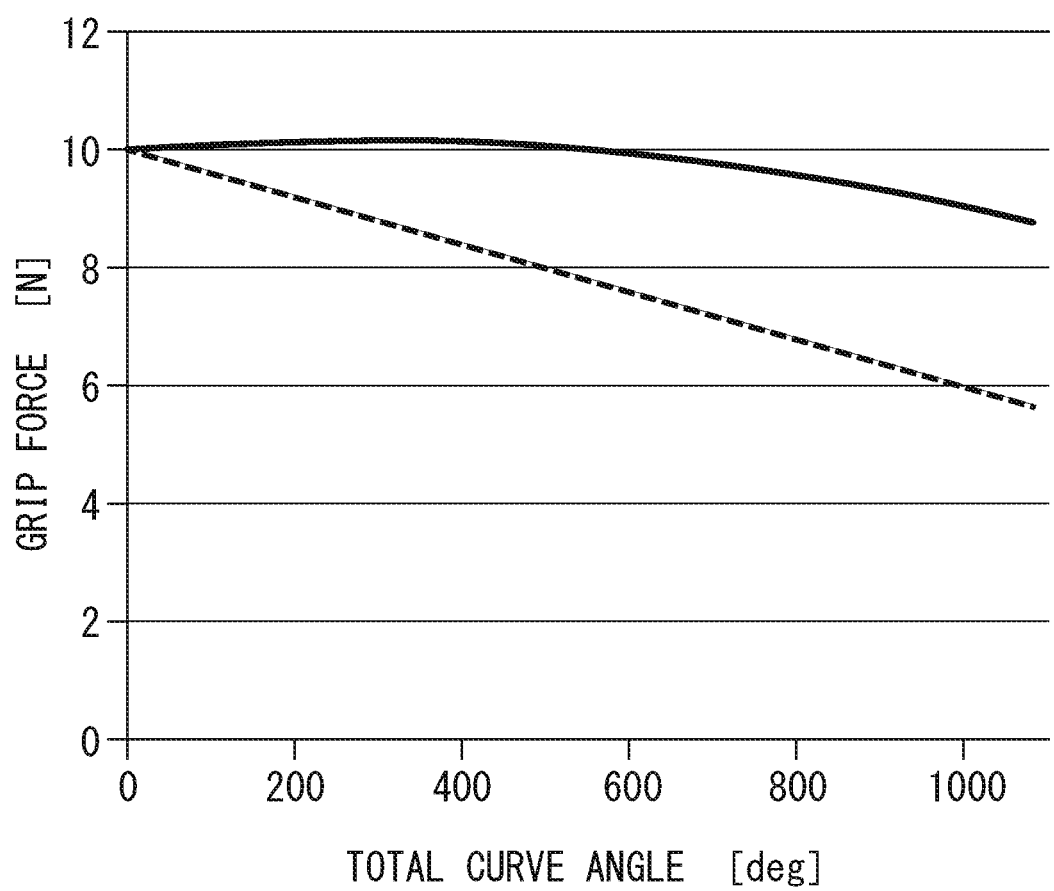
FIG. 5 is a graph showing a relation between a curve angle of the inserting section and the grip force of the end effector in the treatment tool of FIG. 1 (a solid line) and a treatment tool of a comparative example (a broken line).

FIG. 5 is a graph showing one example of a relation between a total curve angle θ of the inserting section 1 and the grip force F, F' of the end effector 2. In FIG. 5, a solid line shows one example of the present embodiment, and a broken line shows a comparative example. In this example, θ=540 (deg), $\Phi b$=0.22 (mm), t=0.2 (mm), and λ=4E−4 (deg$^{-1}$).

As shown by the broken line in FIG. 5, in a case where the power to be input into the proximal end portion of the wire 4 is always constant, the grip force F' noticeably decreases as the curve angle θ of the inserting section 1 increases. On the other hand, as shown by the solid line in FIG. 5, according to the present invention, the grip force F' can be maintained to be almost constant irrespective of the curve angle θ of the inserting section 1.

According to the present embodiment, it is described that the wire 4 is freely movable in the radial direction within the inserting section 1, but instead of this, there may be provided a means that defines a position of the wire 4 in the radial direction within the inserting section 1 so that the wire 4 is always located on a central axis of the inserting section 1 irrespective of the shape of the inserting section 1. For example, as shown in a lower illustration of FIG. 6, an inner sheath 7 having an outer diameter almost equal to an inner diameter of the inserting section 1 and having an inner diameter almost equal to an outer diameter of the wire 4 may be disposed in the inserting section 1, and the wire 4 may be disposed in the inner sheath 7.

Figure 7A:
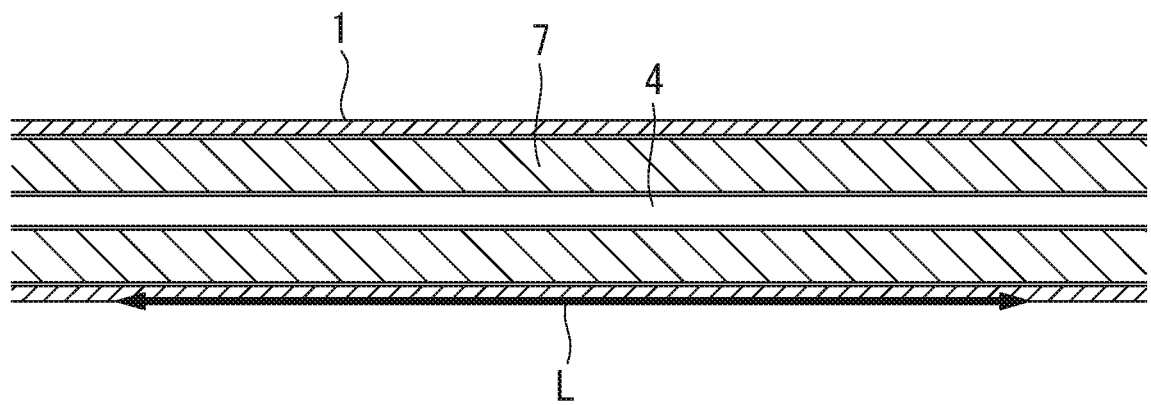
FIG. 7A is an explanatory view of a path length of a wire when an inserting section linearly extends in a treatment tool of the modification of FIG. 6.
Figure 7B:
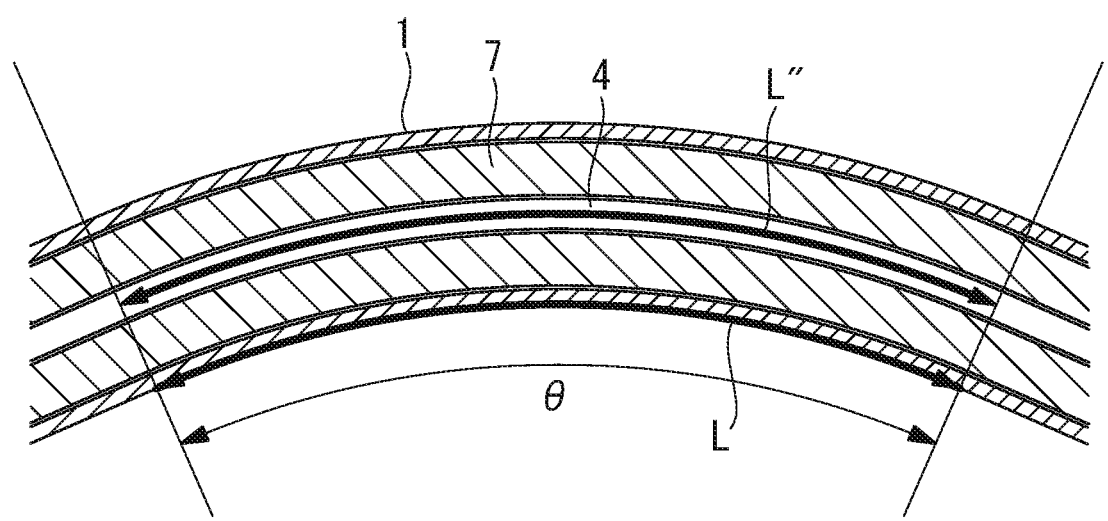
FIG. 7B is an explanatory view of a path length of the wire when the inserting section is curved in the treatment tool of the modification of FIG. 6.

When the wire 4 is disposed on the central axis in the inserting section 1, as shown in FIG. 7A and FIG. 7B, the length L' of the wire 4 in the curved portion of the inserting section 1 is represented by the following equation, and the displacement amount ΔX is represented by $(\Phi a/2+t)\times\theta$. In the following equation, $\Phi a$ is the inner diameter of the inserting section 1.

$$L'=L+(\Phi a/2+t)\times\theta$$

In this case, as compared with a case where the wire 4 is movable in the radial direction within the inserting section 1 (see an upper illustration of FIG. 6), the displacement amount ΔX increases, and the movement amount of the slider 32 from the closed position to the movement limit position therefore increases. This facilitates fine adjustment of the operation of the end effector 2.

Hereinafter, an example of a designed value of the treatment tool 100 according to the present embodiment will be described.

λ=0.0002 to 0.0006 [deg$^{-1}$]
Φa=1 to 5 [mm]
Φb=0.1 to 0.5 [mm] (a case where the inner sheath 7 is provided)
t=0.1 to 1 [mm]
θ=360 to 740 [deg]

When λ=0.0002 [deg$^{-1}$], Φa=5 [mm] (there is the inner sheath), t=1 [mm] and θ=360 [deg], the initial movement amount X of the slider 32 that satisfies Equation (1) is about 272 [mm] that is maximum.

On the other hand, when λ=0.0006 [deg$^{-1}$], Φb=0.1 [mm] (there are not any inner sheaths), t=0.1 [mm] and θ=720 [deg], the initial movement amount X of the slider 32 that satisfies Equation (1) is about 2.47 [mm] that is minimum.

In this way, in consideration of practical design, a position to install the movement regulating section 5 is determined so that the initial movement amount X of the slider 32 is in the following range:

$$2.4 \text{ mm}<X<272 \text{ mm.}$$

The grip force F, F' required for the end effector 2 is in a range of 10 N to 100 N. In the present example, a spring constant k of the elastic member 33 which is required to exert the grip force F, F' of 10 N is about 0.037 [N/mm], and a spring constant k of the elastic member 33 which is required to exert the grip force F, F' of 100 N is about 40 [N/mm]. That is, use of the elastic member 33 having a spring constant of 0.037 [N/mm] or more and 40 [N/mm] or less allows the end effector 2 to exert the grip force F, F' of a size suitable for practical use.

Second Embodiment

Next, description will be hereinafter made as to a treatment tool 200 according to a second embodiment of the present invention with reference to FIG. 8 to FIG. 10.

In the present embodiment, a configuration different from the first embodiment will be described. A configuration common to the first embodiment is denoted with the same reference signs, and description is omitted.

Figure 8:
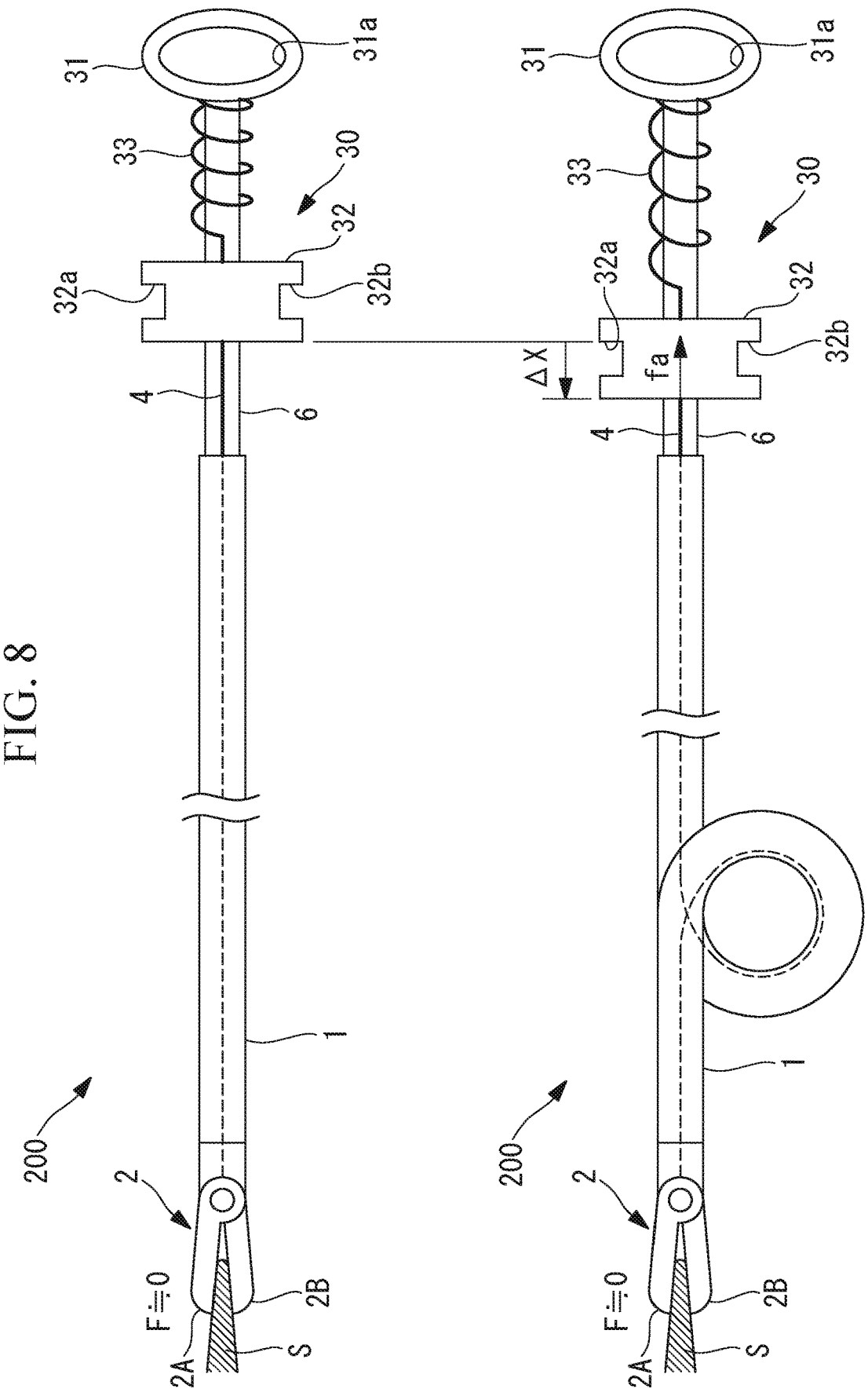
FIG. 8 is an overall configuration view of a treatment tool according to a second embodiment of the present invention, and shows a state where an inserting section linearly extends (an upper illustration) and a state where the inserting section is curved (a lower illustration).

As shown in FIG. 8, the treatment tool 200 according to the present embodiment includes an inserting section 1, an end effector 2, an operating section (a power input section) 30 that is provided on a proximal end side of the inserting section 1 and into which power to drive the end effector 2 is input by an operation of an operator, and a wire 4.

The operating section 30 includes an operating section main body 31, a slider 32, and an elastic member (a power generating portion) 33 disposed between the operating section main body 31 and the slider 32.

A proximal end portion of the wire 4 is fixed to the slider 32. Therefore, in the present embodiment, a pulling force and a pressing force applied to the slider 32 by the operator are directly input into the proximal end portion of the wire 4.

A tip portion of the elastic member 33 is fixed to the slider 32, and a proximal end portion of the elastic member 33 is fixed to the operating section main body 31.

In a state where the inserting section 1 linearly extends (see an upper illustration of FIG. 8), a length of the elastic member 33 is a natural length. On the other hand, in a state where the inserting section 1 is curved (see a lower illustration of FIG. 8), each of the proximal end portion of the wire 4 and the slider 32 is displaced as much as ΔX toward a tip side, and the elastic member 33 accordingly elongates as much as ΔX from the natural length. Therefore, when the inserting section 1 is curved, a pulling force fa=k×ΔX generated by the elastic member 33 is applied to the proximal end portion of the wire 4 via the slider 32. By this pulling force fa of the elastic member 33, a pulling operation of the slider 32 by the operator is assisted.

It is preferable that a pulling force f applied to the slider 32 by the operator to allow the end effector 2 to exert a predetermined amount of grip force F when the inserting section 1 linearly extends is equal to that when the inserting section 1 is curved. That is, it is preferable to satisfy the following equation.

$$f+fa=f/\beta$$

Therefore, a spring constant k of the elastic member 33 is designed to satisfy the following Equation (2). Also in the present embodiment, similarly to the first embodiment, the spring constant k of the elastic member 33 is preferably 0.037 [N/mm] or more and 40 [N/mm] or less.

$$k=(1-\beta)\times f/\Delta X \qquad (2)$$

In this way, according to the present embodiment, in the state where the inserting section 1 is curved, the elastic member 33 generates the pulling force as much as an amount k×ΔX in proportion to a displacement amount ΔX of the proximal end portion of the wire 4, and power to be input into the proximal end portion of the wire 4 increases. This has an advantage that by applying a constant amount of pulling force f to the slider 32 by the operator, the end effector 2 is allowed to exert a constant amount of grip force F irrespective of a curve angle θ of the inserting section 1.

Figure 6:
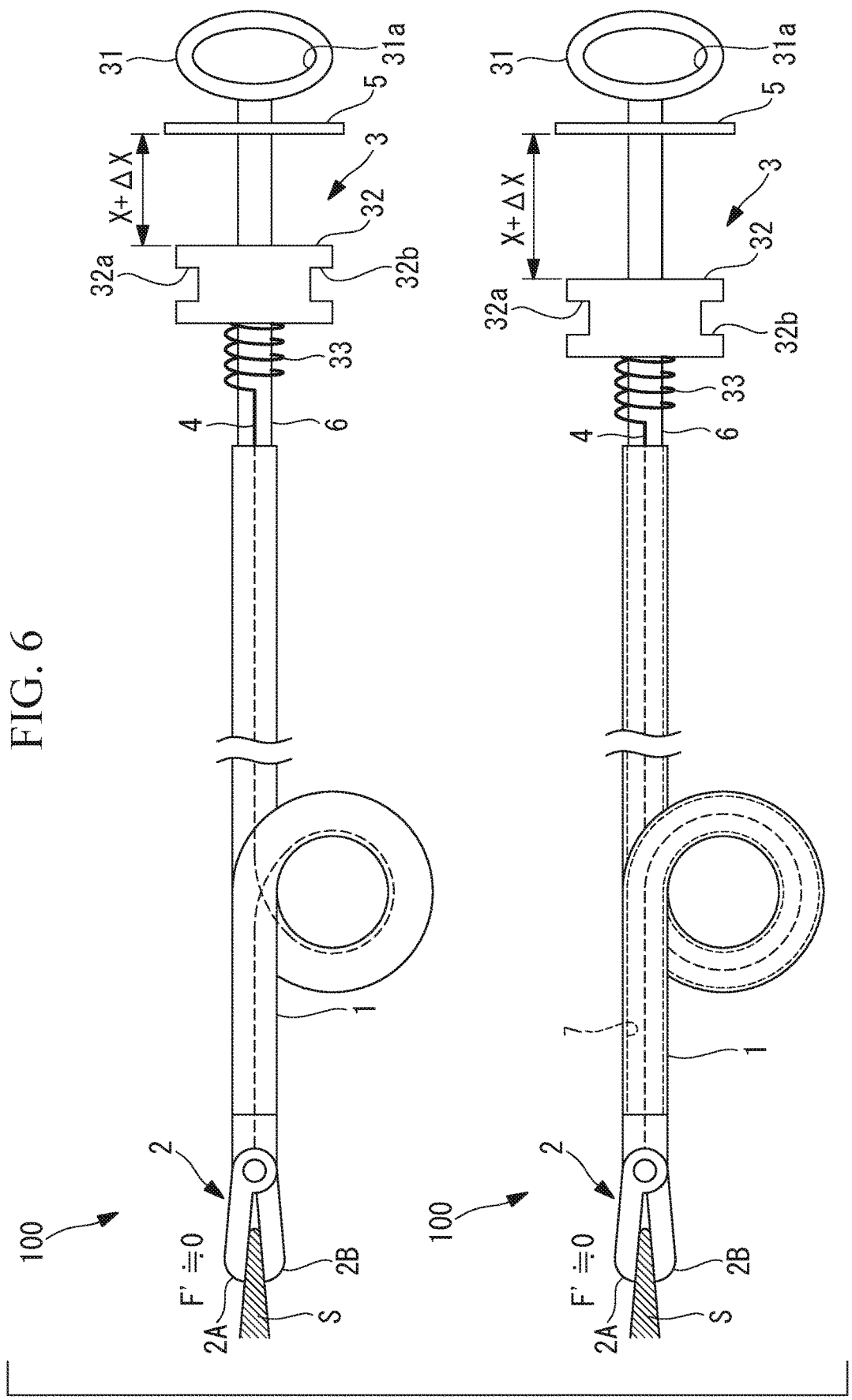
FIG. 6 is an overall configuration view of the treatment tool of FIG. 1 (an upper illustration), and a modification of the treatment tool of FIG. 1 (a lower drawing).

Also in the present embodiment, by providing such an inner sheath 7 as shown in FIG. 6 to FIG. 7B, the wire 4 may be configured to be always located on a central axis of the inserting section 1 irrespective of a shape of the inserting section 1.

Figure 9:
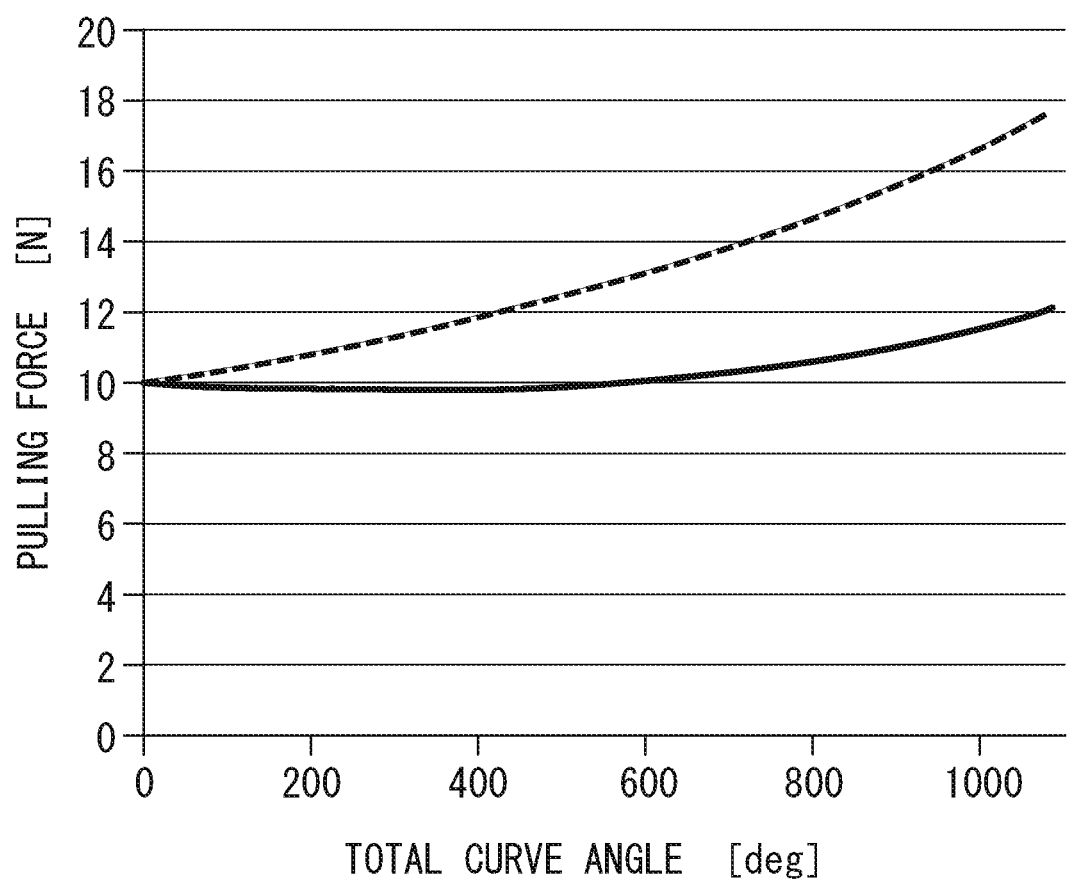
FIG. 9 is a graph showing a relation between a curve angle of the inserting section and a pulling force by an operating section in the treatment tool of FIG. 8 (a solid line) and a treatment tool of a comparative example (a broken line).

FIG. 9 is a graph showing one example of a relation between a total curve angle θ of the inserting section 1 and the pulling force f of the slider 32 required to allow the end effector 2 to exert a constant amount (10 N) of grip force. In FIG. 9, a solid line shows one example of the present embodiment, and a broken line shows a comparative example. In this example, θ=540 (deg), Φb=0.22 (mm), t=0.2 (mm), and λ=4E−4 (deg$^{-1}$).

As shown by the broken line of FIG. 9, in a case where the elastic member 33 is not provided, a required pulling force f increases as a curve angle θ of the inserting section 1 increases. On the other hand, as shown by the solid line of FIG. 9, according to the present embodiment, a constant grip force can be exerted by a constant pulling force f irrespective of the curve angle θ of the inserting section 1.

Figure 10:
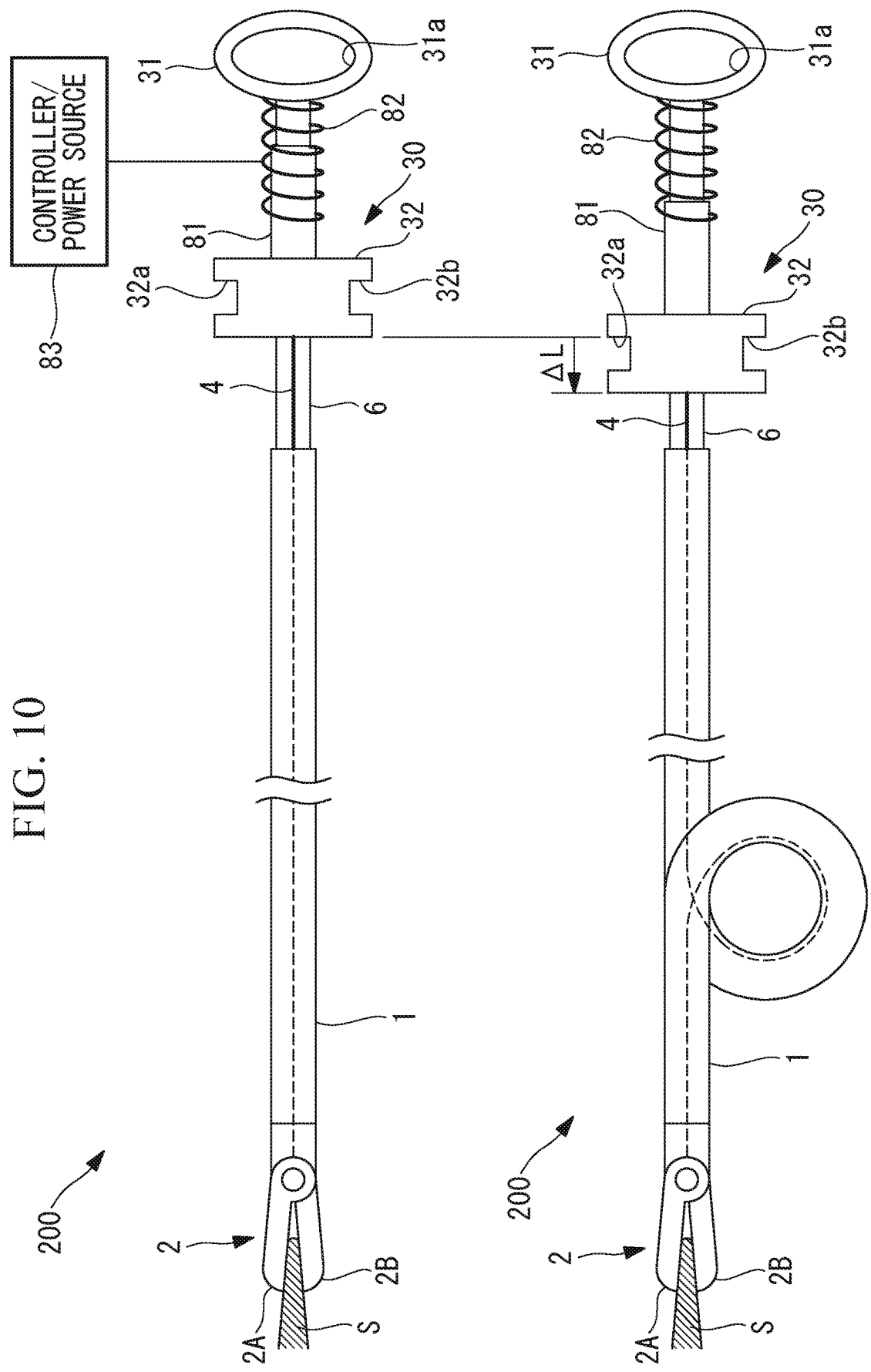
FIG. 10 is an overall configuration view of a modification of the treatment tool of FIG. 8, and shows a state where an inserting section linearly extends (an upper illustration) and a state where the inserting section is curved (a lower illustration).

In the present embodiment, an elastic force of the elastic member 33 is utilized as power that assists the operation of the slider 32 by the operator, but instead of this, a magnetic force that acts on an iron core (a power generating portion) 81 fixed to the slider 32 may be utilized as shown in FIG. 10.

In a modification shown in FIG. 10, a solenoid (a power generating portion) 82 in which the iron core 81 is inserted is fixed to an operating section main body 31, and a controller 83 that controls a current to be supplied to the solenoid 82 is connected to the solenoid 82.

According to the present modification, the iron core 81 is displaced together with a slider 32 by displacement of a wire 4, and self-inductance of the solenoid 82 accordingly changes. The controller 83 detects a displacement amount $\Delta X$ of the wire 4 based on a change amount of the self-inductance of the solenoid 82, and increases the current to be supplied to the solenoid 82 in accordance with the displacement amount $\Delta X$, to increase the magnetic force to be applied to the slider 32 via the iron core 81. Also when the magnetic force is utilized in this way, a pulling operation of the slider 32 by an operator can be assisted.

Third Embodiment

Next, description will be hereinafter made as to a treatment tool 300 according to a third embodiment of the present invention with reference to FIG. 11.

In the present embodiment, a configuration different from the first and second embodiments will be described. A configuration common to the first and second embodiments is denoted with the same reference signs, and description is omitted.

Figure 11:
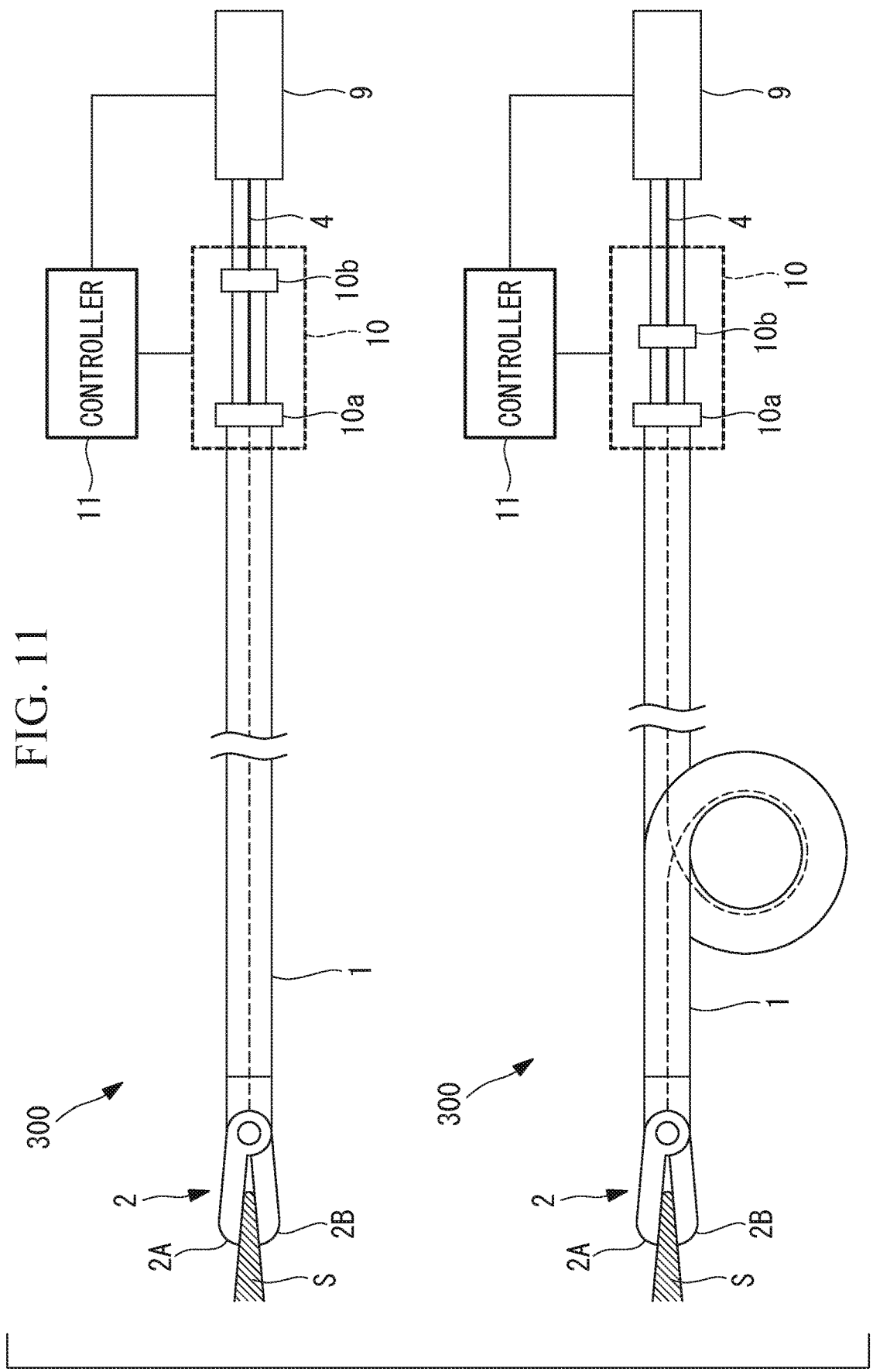
FIG. 11 is an overall configuration view of a treatment tool according to a third embodiment of the present invention, and shows a state where an inserting section linearly extends (an upper illustration) and a state where the inserting section is curved (a lower illustration).

As shown in FIG. 11, the treatment tool 300 according to the present embodiment includes an inserting section 1, an end effector 2, a driving section (a power input section) 9 that is provided on a proximal end side of the inserting section 1 and generates power to drive the end effector 2, a wire 4 that extends through the inserting section 1 and connects the end effector 2 to the driving section 9 to transmit, to the end effector 2, the power input from the driving section 9, a displacement detector 10 that detects a displacement amount of a proximal end portion of the wire 4, and a controller 11 that controls the driving section 9.

The driving section 9 is, for example, a linear actuator, and presses or pulls the proximal end portion of the wire 4 in a longitudinal direction.

The displacement detector 10 measures, for example, a distance between markers 10a and 10b fixed to a proximal end of the inserting section 1 and a middle position of the wire 4 in the longitudinal direction, respectively. When the marker 10b is displaced to a tip side between the proximal end of the inserting section 1 and the driving section 9 by displacement of the wire 4 that accompanies curve of the inserting section 1, as shown in a lower illustration of FIG. 11, the distance between the markers 10a and 10b decreases. Therefore, the displacement detector 10 can detect a displacement amount $\Delta X$ of the proximal end portion of the wire 4 from the distance between the markers 10a and 10b. Information of the detected displacement amount $\Delta X$ of the proximal end portion of the wire 4 is transmitted from the displacement detector 10 to the controller 11.

The controller 11 receives an operation signal to the end effector 2 from an unshown operation input device, and drives the driving section 9 based on the operation signal, thereby causing the end effector 2 to perform an operation corresponding to the operation input into the operation input device. At this time, the controller 11 increases a pulling force to be generated in the driving section 9 in accordance with the displacement amount $\Delta X$ of the proximal end portion of the wire 4, when receiving the operation signal for grip by the end effector 2.

In this way, according to the present embodiment, the pulling force to be input into the proximal end portion of the wire 4 from the driving section 9 in accordance with the displacement amount $\Delta X$ of the proximal end portion of the wire 4 is increased; by the increase of the pulling force, loss of power due to decrease of a power transmission efficiency $\beta$ of the wire 4 can be highly accurately compensated. This has an advantage that irrespective of a curve angle $\theta$ of the inserting section 1, a constant amount of power is applied from a tip portion of the wire 4 to the end effector 2, thereby allowing the end effector 2 to exert a constant amount of grip force.

Figure 12:
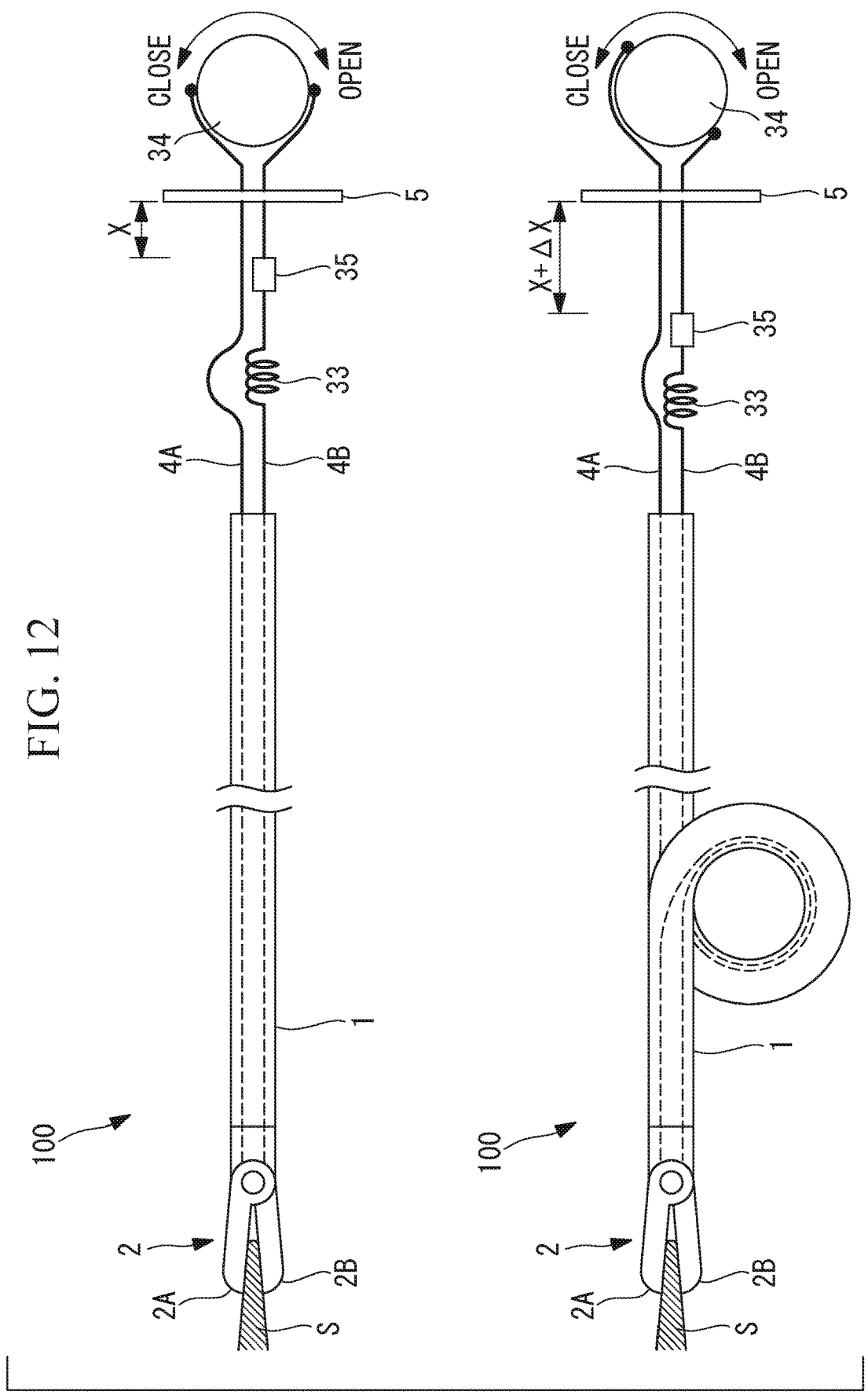
FIG. 12 is an overall configuration view of modifications of the treatment tools according to the first to third embodiments.

In the first to third embodiments, the end effector 2 is opened and closed by pushing and pulling one wire 4, but instead of this, as shown in FIG. 12, a wire 4A for an opening operation and a wire 4B for a closing operation may be separately provided. FIG. 12 shows an example where two wires 4A and 4B are applied to the first embodiment as one example.

Proximal end portions of the two wires 4A and 4B are connected to a common drum (operating member) 34 that is rotatable around an axis in a direction crossing a longitudinal direction of an inserting section 1 and that is rotationally operated by an operator. The opening wire 4A is pulled to a proximal end side by clockwise rotation of the drum 34 to open an end effector 2, and the closing wire 4B is pulled to the proximal end side by counterclockwise rotation of the drum 34 to close the end effector 2. The closing wire 4B is provided with an elastic member 33, and a stopper 35 that abuts on a movement regulating section 5 to limit further pulling of the closing wire 4B by the drum 34.

As shown in an upper illustration of FIG. 12, the opening wire 4A has slack between a proximal end of the inserting section 1 and the drum 34 in a state where the inserting section 1 linearly extends. Consequently, as shown in a lower illustration of FIG. 12, displacement of the opening wire 4A to a tip side is absorbed by deflection in a state where the inserting section 1 is curved.

Figure 13:
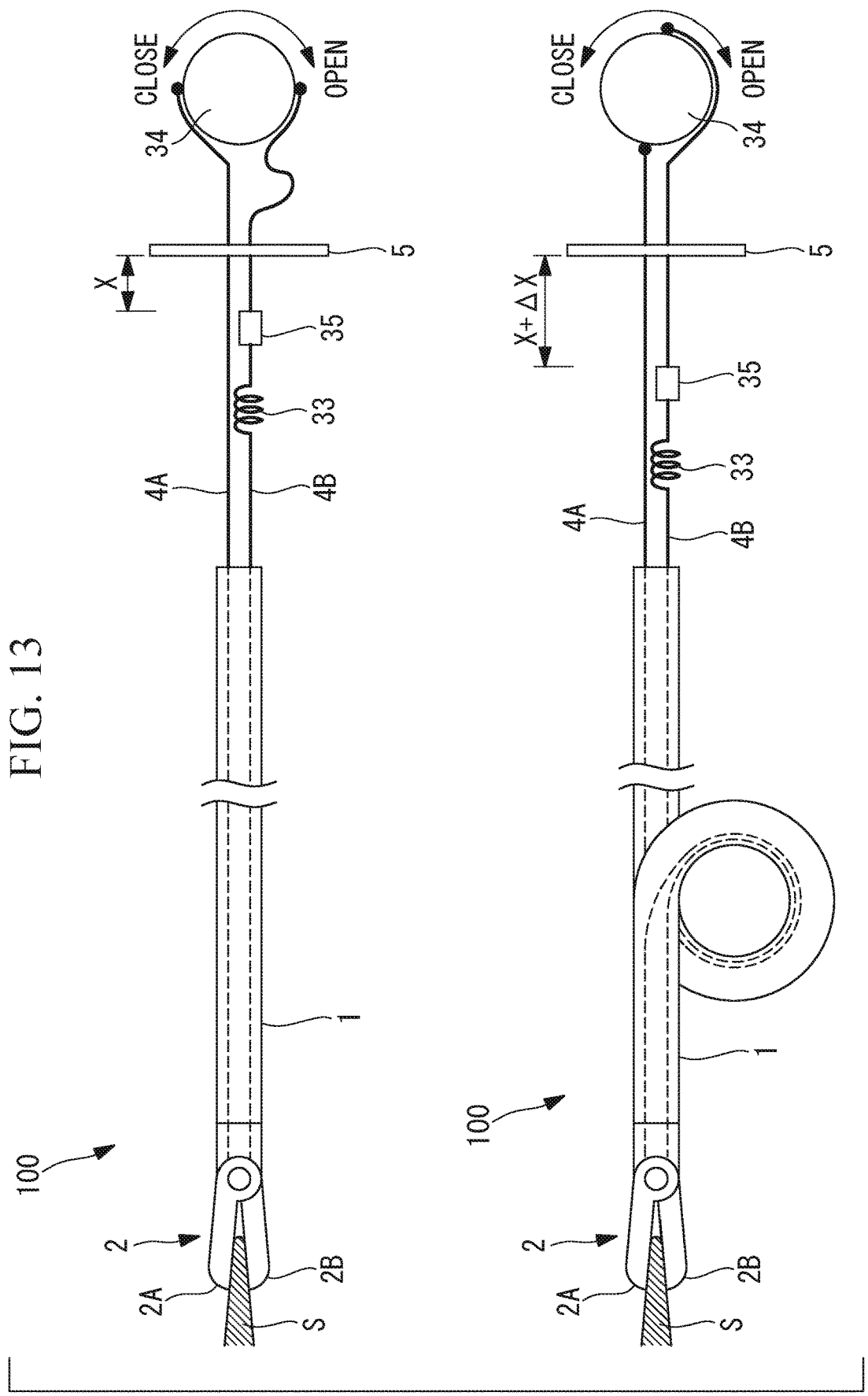
FIG. 13 is an overall configuration view of other modifications of the treatment tools according to the first to third embodiments.

As shown in FIG. 13, in place of an opening wire 4A, a closing wire 4B may have slack between an elastic member 33 and a drum 34.

Figure 14:
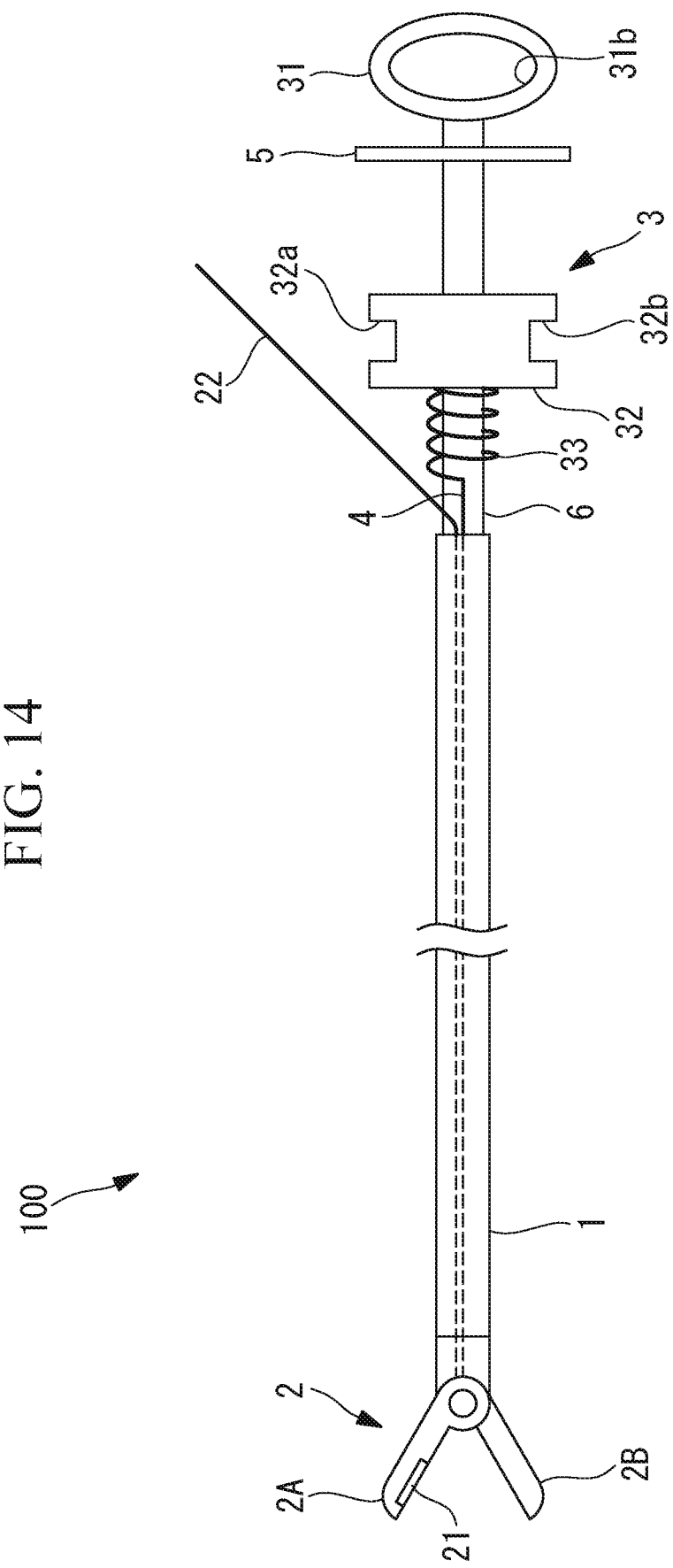
FIG. 14 is an overall configuration view of another modification of the treatment tools according to the first to third embodiments.

In the first to third embodiments, as shown in FIG. 14, the end effector 2 may include an energy release section 21 that releases energy such as heat, an ultrasonic wave or a current, and may include an energy supply member 22, such as an electric wire, that supplies the energy to the energy release section 21. By supplying the energy to the energy release section 21 via the energy supply member 22 from an unshown power source, a treatment of cauterization, incision, coagulation or the like can be performed on a tissue S.

The energy supply member 22 is wired from the end effector 2 through an inserting section 1 to a power source. The energy supply member 22 is drawn out between a proximal end of the inserting section 1 and an elastic member 33 so that the energy supply member 22 does not interfere with the elastic member 33. Alternatively, as shown in FIG. 15, an energy supply member 22 may be passed through a tubular elastic member 33 such as a coil spring, and the energy supply member 22 may be drawn out on a proximal end side of the elastic member 33.

Figure 16:
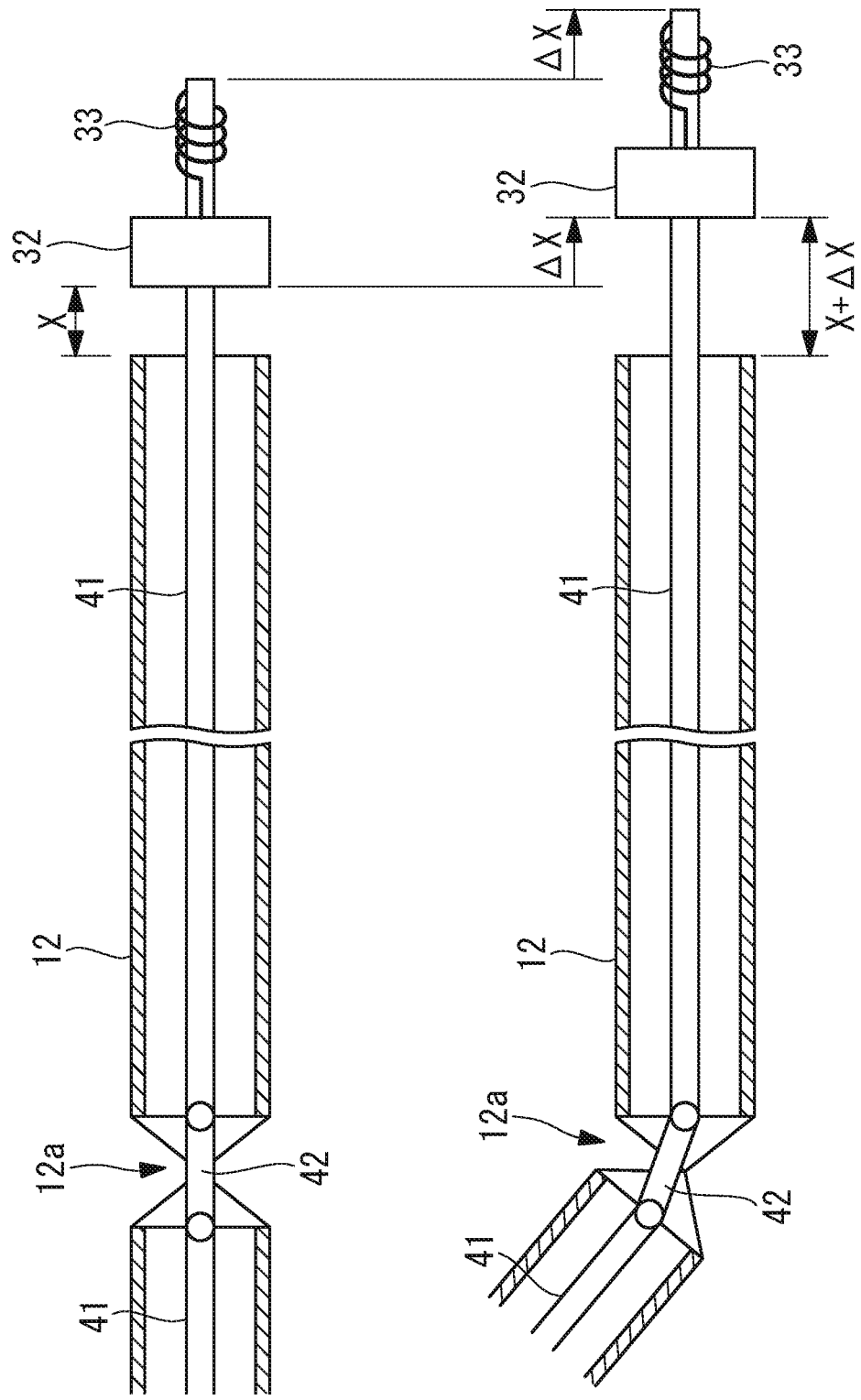
FIG. 16 is an overall configuration view of another modification of the treatment tools according to the first to third embodiments.
Figure 17:
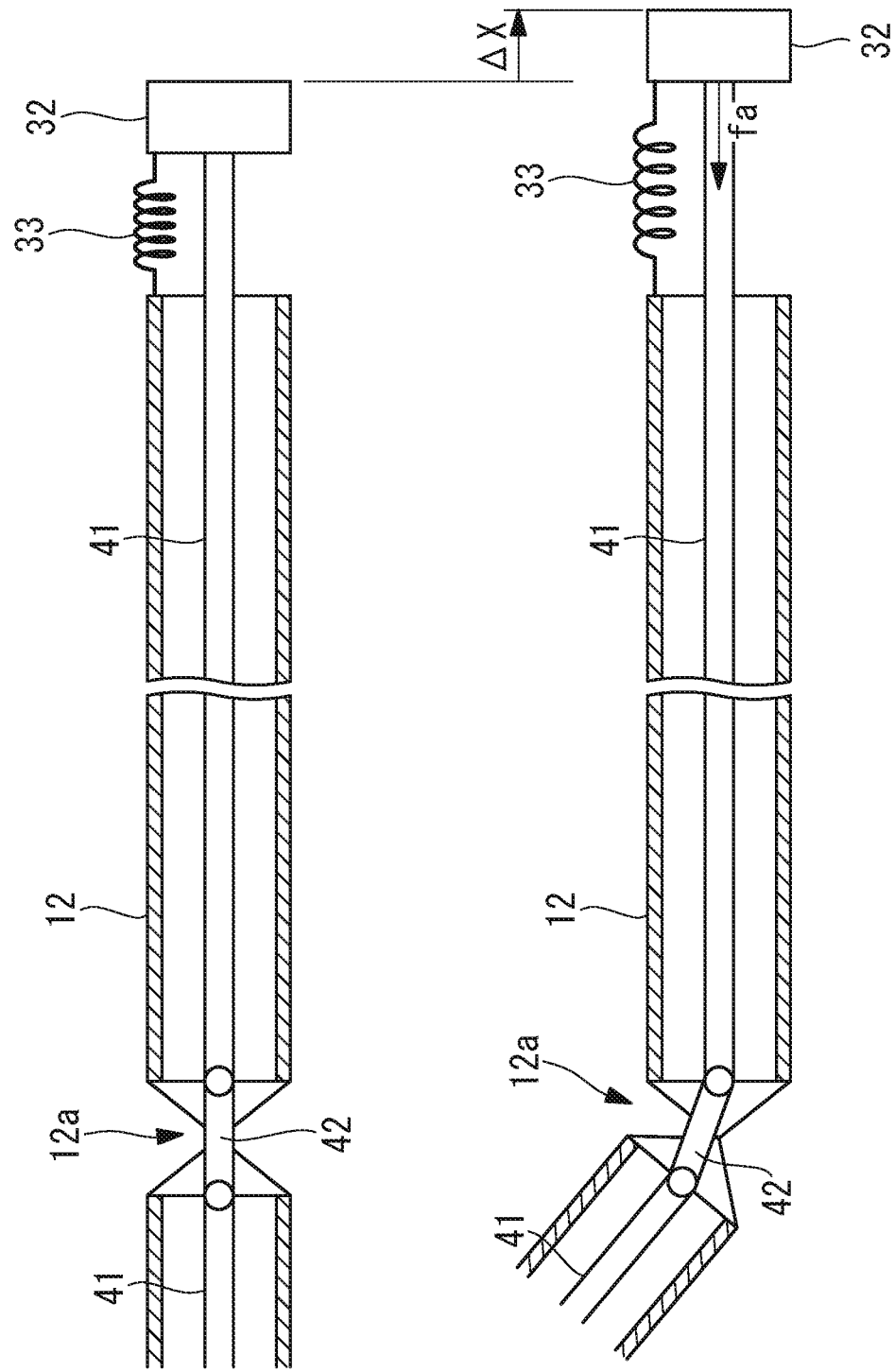
FIG. 17 is an overall configuration view of another modification of the treatment tools according to the first to third embodiments.

In the first to third embodiments, it is described that the inserting section 1 is flexible, but as shown in FIG. 16 and FIG. 17, there may be adopted a hard inserting section 12 having a joint 12a that is bendable around an axis perpendicular to a longitudinal direction. FIG. 16 shows an example where the inserting section 12 is applied to the treatment tool 100 of the first embodiment, and FIG. 17 shows an example where the inserting section 12 is applied to the treatment tool 200 of the second embodiment.

An end effector 2 is connected to an operating section 3 by a plurality of rods 41 coupled to one another via a link 42, in place of the wire 4. The link 42 is provided in the joint 12a, and the link 42 is configured to also bend when the joint 12a bends. When the joint 12a is bent, the rod 41 is displaced on a proximal end side, not on a tip side, by inward displacement of the link 42 in a radial direction. Therefore, in the modifications of FIG. 15 and FIG. 16, the end effector 2 is configured to close by movement of a slider 32 to the tip side.

Figure 15:
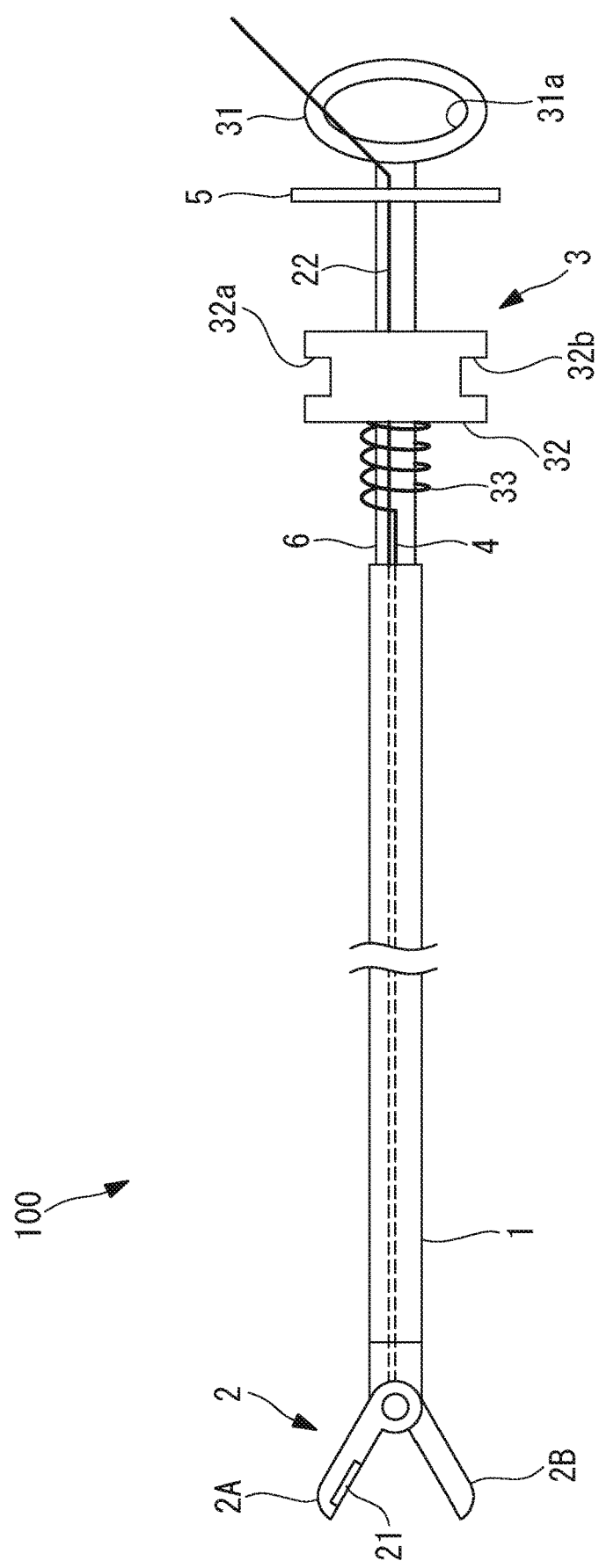
FIG. 15 is an overall configuration view of another modification of the treatment tools according to the first to third embodiments.

Also in the modification of FIG. 15, it is preferable that an initial movement amount X of the slider 32 is designed to satisfy Equation (1) described in the first embodiment. Furthermore, also in the modification of FIG. 16, it is preferable that a spring constant k of the elastic member 33 is designed to satisfy Equation (2) described in the second embodiment.

The above-described embodiment also leads to the following invention.

According to an aspect of the present invention, a treatment tool includes an elongated inserting section that is curveable or bendable, an end effector connected to a tip of the inserting section, an elongated power transmission member that is disposed through the inserting section from the end effector to a proximal end side of the inserting section and transmits, to the end effector, power to drive the end effector, and a power input section that is disposed on the proximal end side of the inserting section and inputs the power to a proximal end portion of the power transmission member, wherein the power input section increases the power to be input into the proximal end portion of the power transmission member in response to displacement of the proximal end portion of the power transmission member in a longitudinal direction, the displacement accompanying a curve or bend of the inserting section.

According to the present aspect, the power input from the power input section into the proximal end portion of the power transmission member is transmitted to the end effector by the power transmission member, thereby allowing the end effector to perform a mechanical operation.

Consequently, when the inserting section is curved or bent, the power transmission member disposed in the inserting section is also curved or bent. Consequently, the proximal end portion of the power transmission member is displaced in the longitudinal direction, and a power transmission efficiency of the power transmission member decreases.

For an angle of the curve or bend of the inserting section, the power transmission efficiency of the power transmission member almost linearly decreases, and the displacement of the proximal end portion of the power transmission member almost linearly increases. That is, an almost linear relation is present between the decrease of the power transmission efficiency of the power transmission member and the displacement of the proximal end portion of the power transmission member. Therefore, the input of the power increases in response to the displacement of the proximal end portion of the power transmission member, so that loss of power due to the decrease of the power transmission efficiency can be favorably compensated by the increase of the input of the power. Consequently, a certain amount of power can be transmitted to the end effector irrespective of the curve or bend of the inserting section.

In the above aspect, the power input section may include an operation member that is connected to the proximal end portion of the power transmission member, and is operated in the longitudinal direction by an operator to input, into the proximal end portion of the power transmission member, the power based on an operation amount, and a maximum operation amount of the operation member may be increased by the displacement of the proximal end portion of the power transmission member.

Consequently, when the inserting section is curved or bent, larger power can be input into the proximal end portion of the power transmission member via the operation member by the operator to compensate for the loss of power in the power transmission member.

In the above aspect, the power input section may include an elastic member that connects the proximal end portion of the power transmission member to the operation member, and generates an elastic force in a reverse direction to a direction of the displacement of the proximal end portion of the power transmission member by an operation of the operation member, and the treatment tool may include a movement regulating section that regulates the operation amount of the operation member.

Consequently, the elastic force generated by elastically deforming the elastic member by the operation of the operation member can be input as the power into the proximal end portion of the power transmission member. Furthermore, when the inserting section is curved or bent, an elastically deformable amount of the elastic member is increased by the displacement of the proximal end portion of the power transmission member. Therefore, the power that can be input into the proximal end portion of the power transmission member can be increased. Furthermore, the operation amount of the operation member is regulated by the movement regulating section, so that a size of the power that can be input into the proximal end portion of the power transmission member via the operation member by the operator can be limited to be less than or equal to a predetermined value.

In the above aspect, the movement regulating section may regulate, in the following range, the operation amount X of the operation member in a state where the inserting section linearly extends:

$$2.4\ \text{mm} < X < 272\ \text{mm}.$$

Consequently, such design can be suitable for a small-diameter inserting section to be inserted into a body.

In the above aspect, the treatment tool may include two power transmission members each of which transmits power to the end effector, the operation member and the elastic member may be connected to a proximal end portion of one of the two power transmission members, and in a state where the inserting section linearly extends, the one power transmission member may have slack between the elastic member and the operation member, or the other power transmission member may have slack.

Consequently, two operations (e.g., an opening operation and a closing operation) of the end effector can be controlled via two power transmission members, respectively.

In the above aspect, the power input section may include a power generating portion that is connected to the proximal end portion of the power transmission member, and generates power in a reverse direction to a direction of the displacement of the proximal end portion of the power transmission member by the displacement of the proximal end portion of the power transmission member, the displacement accompanying the curve or bend of the inserting section.

Consequently, when the proximal end portion of the power transmission member is displaced, the power in the reverse direction to the direction of the displacement of the proximal end portion of the power transmission member is applied from the power generating portion to the proximal end portion of the power transmission member. In consequence, the power to be input into the proximal end portion of the power transmission member can be increased.

In the above aspect, the power generating portion may include an elastic member that is elastically deformable in the longitudinal direction.

Consequently, the elastic member elastically deformed by the displacement of the proximal end portion of the power transmission member generates an elastic force in a reverse direction to the direction of the displacement of the proximal end portion of the power transmission member, and this elastic force is applied to the proximal end portion of the power transmission member. The elastic force of the elastic member is proportional to an elastically deformed amount, that is, a displacement amount of the proximal end portion of the power transmission member. Therefore, the power to be input into the proximal end portion of the power transmission member is increased by the elastic force of the elastic member, so that loss of power in the power transmission member can be highly accurately compensated.

In the above aspect, the elastic member may have a spring constant of 0.037 N/mm or more and 40 N/mm or less.

Consequently, a size of the power to be generated by the elastic member can be controlled in a range that is suitable for a small-diameter inserting section to be inserted into a body.

In the above aspect, a surface of the power transmission member may be coated with a high slidability material.

In this way, friction between the power transmission member and a peripheral member is decreased to increase slidability of the power transmission member, so that linearity between the decrease of the power transmission efficiency of the power transmission member and the displacement of the proximal end portion of the power transmission member further increases. This can further accurately compensate for the loss of power based on the displacement amount of the proximal end portion of the power transmission member.

In the above aspect, the end effector may include an energy release section that releases energy, and may include an energy supply member that supplies the energy to the energy release section.

Consequently, by supplying the energy from the energy supply member, the energy is released from the energy release section to a tissue, so that a treatment of cauterization, incision, coagulation or the like can be performed.

REFERENCE SIGNS LIST 100, 200 and 300 treatment tool
1 and 12 inserting section
12a joint
2 end effector
21 energy release section
22 energy supply member
2A and 2B grip piece
3 operating section (a power input section)
31 operating section main body
32 slider (an operation member)
33 elastic member (a power generating portion)
4 wire (a power transmission member)
41 rod (a power transmission member)
42 link
5 movement regulating section
7 inner sheath
81 iron core (a power generating portion)
82 solenoid (a power generating portion)
9 driving section (a power input section)
10 displacement detector
11 controller

The invention claimed is:

1. A treatment tool comprising:
an elongated inserting section configured to be curved or bent;
an end effector connected to a distal end of the inserting section;
at least one wire disposed from the end effector to a proximal end side of the inserting section through the inserting section;
an operating section main body;
a slider connected to a proximal end portion of the at least one wire, the slider being configured to be movable relative to the operating section main body in a direction along a longitudinal direction of the inserting section to apply a grip force to the end effector; and
a spring connected between a proximal end of the slider and the operating section main body at a position on the operating section main body proximal to the proximal end of the slider,
wherein as a result of the inserting section being curved or bent, the slider reacts by moving distally and the spring reacts by biasing the slider in a proximal direction to prevent a decrease in the grip force when the inserting section is curved or bent.

2. The treatment tool according to claim 1, wherein wherein an operation amount of the slider, in a state where the inserting section is linear, is set to a predetermined value to allow the end effector to apply a certain grip force irrespective of the curve or the bend of the inserting section.

3. The treatment tool according to claim 2, further comprising a stop configured to limit the operation amount of the slider.

4. The treatment tool according to claim 3, wherein the stop limits the operation amount of the slider in the state where the inserting section is linear to between 2.4 mm and 272 mm.

5. The treatment tool according to claim 3, wherein:
the at least one wire is two wires each of which transmits power to the end effector,
the slider and the spring are connected to the proximal end portion of one of the two wires, and
in the state where the inserting section is linear, one of the two wires has slack between the spring and the slider.

6. The treatment tool according to claim 1, wherein the spring is configured to generate power in the proximal direction when the inserting section is curved or bent.

7. The treatment tool according to claim 6, wherein the spring comprises a helical extension spring configured to be elastically deformable in the longitudinal direction.

8. The treatment tool according to claim 1, wherein the spring has a spring constant of 0.037 N/mm or more and 40 N/mm or less.

9. The treatment tool according to claim 1, wherein a surface of the at least one wire is coated with a material for reducing friction relative to an uncoated portion of the at least one wire.

10. The treatment tool according to claim 1, wherein
the end effector comprises an energy release section that releases energy, and
the treatment tool comprises an electric wire that supplies the energy to the energy release section.

11. A treatment tool comprising:
an elongated inserting section configured to be curved or bent;
an end effector connected to a distal end of the inserting section configuring to apply a grip force;
at least one wire disposed from the end effector to a proximal end side of the inserting section through the inserting section; and
a power input section configured to bias a proximal end of the at least one wire proximally;
wherein as a result of the inserting section being curved or bent, the power input section is configured to react by increasing power input to the proximal end of the at least one wire in response to displacement of the proximal end of the at least one wire in a longitudinal direction to prevent a decrease in the grip force when the inserting section is curved or bent.

12. The treatment tool according to claim 11, wherein the power input section comprises:
an operating section main body;
a slider connected to the proximal end of the at least one wire, the slider being configured to be movable relative to the operating section main body in a direction along the longitudinal direction of the inserting section to actuate the end effector; and
a spring connected between a proximal end of the slider and the operating section main body at a position on the operating section main body proximal to the proximal end of the slider, the spring being configured to bias the slider proximally.

13. The treatment tool according to claim 11, wherein
the at least one wire comprises a first wire and a second wire each disposed from the end effector to the proximal end side of the inserting section through the inserting section, the first wire and the second wire each being elongated along a longitudinal axis; and
the power input section comprising:
a spring disposed on the first wire;
a pulley rotatable about an axis offset from the longitudinal axis, the pulley being connected to a proximal end of each of the first wire and the second wire;
wherein the power input section is configured to increase the power input into a proximal end portion of the first wire in response to displacement of the proximal end portion of the first wire in the longitudinal direction when the inserting section is curved or bent.

14. The treatment tool according to claim 13, wherein in a state where the inserting section is linear, one of the first wire or the second wire is configured to have slack between the spring and the pulley.

15. The treatment tool according to claim 13, wherein the axis is orthogonal relative to the longitudinal axis.

* * * * *